(12) United States Patent
Guo et al.

(10) Patent No.: US 9,486,790 B2
(45) Date of Patent: Nov. 8, 2016

(54) MODIFICATION METHOD OF TITANIUM-SILICALITE ZEOLITE BASED ON THE MIXTURE OF QUATERNARY AMMONIUM SALT AND INORGANIC ALKALI

(75) Inventors: Hongchen Guo, Liaoning (CN); Ji Su, Liaoning (CN); Guanghong Liu, Liaoning (CN)

(73) Assignee: DALIAN UNIVERSITY OF TECHNOLOGY, Liaoning (CN)

( * ) Notice: Subject to any disclaimer, the term of this patent is extended or adjusted under 35 U.S.C. 154(b) by 378 days.

(21) Appl. No.: 14/355,157

(22) PCT Filed: Mar. 18, 2012

(86) PCT No.: PCT/CN2012/072499
§ 371 (c)(1),
(2), (4) Date: Apr. 29, 2014

(87) PCT Pub. No.: WO2013/063893
PCT Pub. Date: May 10, 2013

(65) Prior Publication Data
US 2014/0301942 A1    Oct. 9, 2014

(30) Foreign Application Priority Data

Oct. 31, 2011    (CN) .......................... 2011 1 0338451

(51) Int. Cl.
| | |
|---|---|
| C01B 39/08 | (2006.01) |
| B01J 29/89 | (2006.01) |
| B01J 29/04 | (2006.01) |
| C07D 301/03 | (2006.01) |
| C07D 303/04 | (2006.01) |
| B01J 29/035 | (2006.01) |
| C01B 37/00 | (2006.01) |

(52) U.S. Cl.
CPC ............. B01J 29/041 (2013.01); B01J 29/035 (2013.01); B01J 29/89 (2013.01); C01B 37/005 (2013.01); C01B 39/085 (2013.01); C07D 301/03 (2013.01); C07D 303/04 (2013.01); *B01J 2229/183* (2013.01); *B01J 2229/34* (2013.01); *B01J 2229/38* (2013.01)

(58) Field of Classification Search
CPC ... C01B 39/085; B01J 29/89; B01J 2229/34; B01J 2229/38; B01J 2229/183
See application file for complete search history.

(56) References Cited

U.S. PATENT DOCUMENTS

| | | | |
|---|---|---|---|
| 4,410,501 A | 10/1983 | Taramasso et al. | |
| 4,794,198 A | 12/1988 | Roffia et al. | |
| 5,365,003 A | 11/1994 | Chang et al. | |
| 5,367,099 A | 11/1994 | Beck et al. | |
| 5,476,823 A | 12/1995 | Beck et al. | |
| 5,607,888 A | 3/1997 | Chang et al. | |
| 5,656,252 A | 8/1997 | Tuel et al. | |
| 5,688,484 A | 11/1997 | Saxton et al. | |
| 6,475,465 B2 | 11/2002 | Lin et al. | |
| 2009/0221725 A1 | 9/2009 | Chornet et al. | |

FOREIGN PATENT DOCUMENTS

| | | |
|---|---|---|
| CM | 101665256 A | 3/2010 |
| CN | 1167010 A | 12/1997 |
| CN | 1167082 A | 12/1997 |
| CN | 1169952 A | 1/1998 |
| CN | 1217232 A | 5/1999 |
| CN | 1239015 A | 12/1999 |
| CN | 1239016 A | 12/1999 |
| CN | 1245089 A | 2/2000 |
| CN | 1245090 A | 2/2000 |
| CN | 1247771 A | 3/2000 |
| CN | 1260241 A | 7/2000 |
| CN | 1268400 A | 10/2000 |
| CN | 1275529 A | 12/2000 |
| CN | 1275530 A | 12/2000 |
| CN | 1294030 A | 5/2001 |
| CN | 1301599 A | 7/2001 |
| CN | 1327947 A | 12/2001 |
| CN | 1328878 A | 1/2002 |
| CN | 1418813 A | 5/2003 |
| CN | 1421389 A | 6/2003 |
| CN | 1482062 A | 3/2004 |
| CN | 1488438 A | 4/2004 |
| CN | 1513760 A | 7/2004 |
| CN | 1555923 A | 12/2004 |
| CN | 1634765 A | 7/2005 |
| CN | 1216801 C | 8/2005 |
| CN | 1657168 A | 8/2005 |
| CN | 1775360 A | 5/2006 |
| CN | 1806918 A | 7/2006 |
| CN | 1830564 A | 9/2006 |
| CN | 1843626 A | 10/2006 |
| CN | 1844321 A | 10/2006 |
| CN | 1935651 A | 3/2007 |

(Continued)

*Primary Examiner* — David M Brunsman
(74) *Attorney, Agent, or Firm* — Muncy, Geissler, Olds & Lowe, P.C.

(57) ABSTRACT

This invention relates to a modification method for titanium-silicalite zeolite (TS-1). The feature of the invention is pretreating the TS-1, after that the TS-1 is modified by the mixture of quaternary ammonium salts and inorganic base. The quaternary ammonium salts mentioned above include tetrapropylammonium fluoride, tetrapropylammonium chloride, tetrapropylammonium iodide and their mixture. The inorganic base includes LiOH, NaOH and KOH and their mixtures. TS-1 after the modification is aftertreated at last. The invention is universal capable to modify the TS-1 synthesized by any method, especially the TS-1 made with a low cost method. The modification can enhance the catalytic performance on both gas and liquid phase epoxidation of propylene.

5 Claims, No Drawings

(56) References Cited

FOREIGN PATENT DOCUMENTS

| | | | |
|---|---|---|---|
| CN | 101134575 | A | 3/2008 |
| CN | 101190792 | A | 6/2008 |
| CN | 101190793 | A | 6/2008 |
| CN | 101291877 | A | 10/2008 |
| CN | 101327934 | A | 12/2008 |
| CN | 101417238 | A | 4/2009 |
| CN | 101428814 | A | 5/2009 |
| CN | 101434399 | A | 5/2009 |
| CN | 101434400 | A | 5/2009 |
| CN | 101537372 | A | 9/2009 |
| CN | 101591024 | A | 12/2009 |
| CN | 101602013 | A | 12/2009 |
| CN | 101618338 | A | 1/2010 |
| CN | 101618339 | A | 1/2010 |
| CN | 101623653 | A | 1/2010 |
| CN | 101656798 | A | 3/2010 |
| CN | 101658791 | A | 3/2010 |
| CN | 101659599 | A | 3/2010 |
| CN | 101670298 | A | 3/2010 |
| CN | 101696019 | A | 4/2010 |
| CN | 101757945 | A | 6/2010 |
| CN | 101767036 | A | 7/2010 |
| CN | 101786638 | A | 7/2010 |
| CN | 101850985 | A | 10/2010 |
| CN | 101850986 | A | 10/2010 |
| CN | 101850986 | * | 8/2012 |
| EP | 0958861 | A1 | 11/1999 |
| EP | 1830427 | A1 | 9/2007 |
| JP | 57-130938 | A | 8/1982 |
| JP | 63-27445 | A | 2/1988 |
| JP | 2003-34632 | A | 2/2003 |
| JP | 5046463 | B2 | 10/2012 |
| WO | WO 2008/090268 | A1 | 7/2008 |
| WO | WO 2009/077086 | A1 | 6/2009 |
| WO | WO 2009/126765 | A2 | 10/2009 |

* cited by examiner

MODIFICATION METHOD OF TITANIUM-SILICALITE ZEOLITE BASED ON THE MIXTURE OF QUATERNARY AMMONIUM SALT AND INORGANIC ALKALI

FIELD OF THE INVENTION

This invention belongs to the technical field of inorganic chemical synthesis, relating to a modification method for titanium-silicalite zeolite (TS-1).

BACKGROUND OF THE INVENTION

Titanium-silicalite (TS-1) is a zeolite with transition metal Ti in the framework and MFI framework topology, characterized by good selective oxidation and shape-selectivity. Associated with environmentally-attractive oxidant, aqueous $H_2O_2$, TS-1 has been widely applied in selective, catalytic oxidation of organic compounds, such as alcohols, phenols, olefins and ethers, etc. In particular, hydroxylation of phenol, oxidation of cyclohexanone amine and propylene epoxidation have been realized in industrial production.

Since 1981, the synthetic method of TS-1 was firstly published by Macro Taramasso. In the following three decades, hydrothermal synthesis of TS-1 has formed two types through continuous development. One is the adoption of tetrapropylammonium hydroxide (TPAOH) as template to synthesize TS-1 (classic method). The following patents and publications belong to the classic method: U.S. Pat. No. 5,656,252, WO2009077086, CN1167082A, CN 1260241A, CN 1169952A, CN 1239016A, CN1217232A, CN 1239015A, CN1245089A, CN 1247771A, CN1275530A, CN1275529A, CN1294030A, CN1328878A, CN1327947A, CN1418813A, CN1216801C, CN 1488438A, CN 1482062A, CN1634765A, CN 1843626A, CN 1830564A, CN 101134575A, CN101291877A, CN1935651A, CN101190792A, CN101190793A, CN 101434399A, CN101434400A, CN101327934A and CN101696019A, etc.; and Zeolites 12(1992)943-950, Zeolites 16(1996)184-195, Zeolites 19(1997)238-245, Microporous and Mesoporous Materials 22(1998)23-31, Microporous and Mesoporous Material 66(2003)143-156 and Chemical Engineering Journal 147(2009)316-322, etc. Another one is the use of a relatively low price tetrapropylammonium bromide (TPABr) or other inexpensive templates to synthesize the TS-1 system (low-cost method). The following patents and publications belong to the low-cost method: U.S. Pat. No. 5,688,484, CN1167010A, CN 1513760A, CN1806918A, CN 101428814A and CN101767036A, etc.; and Material Chemistry and Physics 47(1997)225-230, Zeolites 19(1997)246-252, Microporous and Mesoporous Materials 12(1997)141-148, Catalysis Today 74(2002)65-75, Applied Catalysis A 185(1999)11 and Chinese Journal of Catalysis 17(1996)173-176, etc.

Besides two above-mentioned hydrothermal synthesis, TS-1 can be synthesized by a variety of methods, such as isomorphous substitution, etc. But owing to the longer bond distance of Ti—O than that of Si—O, it is difficult for Ti atom to be introduced into the framework of zeolite. Therefore, no matter which method used in synthesis of TS-1 would form some non-framework titanium species. The existence of non-framework titanium species would generate two negative effects on the production of TS-1. The first one is these non-framework titanium species have no catalytic activity, but would trigger the decomposition of oxidant hydrogen peroxide. Thus during the reaction it would reduce the catalytic performance of TS-1. The second one is the amount of non-framework titanium species is hard to control, which would results in the different catalytic performance of TS-1 from different synthesis batch.

In order to reduce the bad influence of non-framework titanium species, the following patents and publications are about the modification of TS-1.

U.S. Pat. No. 5,367,099, U.S. Pat. No. 5,607,888, U.S. Pat. No. 5,476,823, U.S. Pat. No. 5,365,003, CN101602013A and CN1844321A introduce a silane modified method for zeolite with MFI topology. A representative patent CN101602013A discloses a silane modified method in gas phase for TS-1, in which the silylation agent under nitrogen atmosphere was introduced into the reaction for 0.5-10 h at 50-300° C.

Patents CN1245090A, U.S. Pat. No. 4,794,198, CN1657168A, CN101591024A and CN101417238A introduce an acid treatment for TS-1. A representative patent CN1657168A discloses an acid treatment for uncalcinated TS-1, in which uncalcinated TS-1 was mixed with acidic solution under room temperature to 200° C., then the regular filtration, wash, drying and calcination were performed.

Patents CN1555923A, CN1268400A, CN101659599A and EP0958861 A1, and publications Catalysis Today 93-95 (2004)353-357 and Chemical Engineering (China) Vol39, No1, P53-57 introduce a salt modification for TS-1. A representative patent CN1268400A discloses a modified method by using aqueous solution of a metal salt or mixtures, in which according to the ratio of metal salt:water: zeolite=0.01-10 g:10-100 ml:1 g, TS-1 was added into the aqueous solution of metal salt, and keep the mixture in static state for 6-100 h, then dry it at 30-100° C. by using water bath and further dry it at 110-200° C. in oven for 1-20 h. At last using temperature programmed method to increase temperature from 200 to 800° C. about 1-12 h, the zeolite was calcinated about 2-20 h at this temperature.

The above three modification methods can increase the certain catalytic performance of TS-1. The modification by acid and salt can suppress the negative influence of non-framework of titanium species during the reaction. However, all of these methods cannot essentially eliminate it.

It is reported that inorganic or organic alkalic solution modification of TS-1 can generate holes in TS-1, which is in favor of diffusion of reactants and products.

The following patents introduce modification method of TS-1 by using inorganic or organic alkalic solution.

U.S. Pat. No. 6,475,465B2 and CN1301599A (application date Dec. 24, 1999; application number 99126289.1) both disclose a modification method using organic alkalic solution, in which according to the ratio of organic alkalic solution (such as aliphatic amines, alcohol amines, quaternary ammonium compounds) or mixtures (mol):TS-1 (g): water (mol)=(0.005-0.5):100:(5-200), to make them mixed and reacted under 150-180° C. for 2 hours to 3 days. The TS-1 zeolite used here can be the raw or acidic modified TS-1.

Patent CN124090A (application date Aug. 18, 1998, application number 98117503.1) discloses a further modification method using organic alkalic solution for acidic-modified TS-1 sample, in which the mixture of TS-1 sample and acidic solution reacted for 5 min to 6 h under 5-95° C. Then, the acidic-modified TS-1 sample and organic alkalic solution were mixed, and reacted in sealed reactor for 2 h to 8 days under 120-200° C. and autogenous pressure. The organic alkali used here can be aliphatic amines, alcohols amines, quaternary ammonium compounds, etc., or the mixture of these organic alkali.

Patent CN101850985A (application date Mar. 31, 1998, application number 200910131993.5) discloses a method using alkaline solution of pore former to modify TS-1 sample. In this method, TS-1 sample was added into alkaline solution of pore former, the mixture with the ratio of TS-1:pore former:alkali:water=100:(0.001-5):(0.005-5):(200-10000) was attained. Then the mixture reacted for 2-360 h under 80-200° C. and autogenous pressure. The pore former can be sucrose, starch, furfural, phenol, benzothiophene, dibenzothiophene, naphthyl, quinoline, carbazole, indole, polypropylene, polyethylene glycol, polystyrene, polyvinyl chloride, polyethylene and the mixtures or derivatives of these compounds. The alkaline source can be divided into organic or inorganic alkali, in which organic alkali can be urea, quaternary ammonium hydroxides compounds, aliphatic amines, alcohols amines and the mixture of these compounds; inorganic alkali can be ammonia, sodium hydroxide, potassium hydroxide, barium hydroxide and the mixture of these compounds.

Patent CN101537372A, CN101618338A, CN101618339A, CN101623653A, 101658791A, CN101658798A, CN1016646696A, CN101665256A and CN101670298A disclose a modification method for TS-1 using alkaline solution involving noble metal. In this method, the mixture of TS-1, aqueous solution of silicon, noble metal source, protective agent and alkaline source was hydrothermally reacted in sealed reactor, and recycled the products. The noble metal source can be the oxides, halides, carbonates, nitrates, ammonium salts and hydroxides of Ru, Rh, Pd, Re, Os, Ir, Pt, Ag and Au, or other compounds of these metal. Protective agent can be glucose, cyclodextrin, polybenzimidazole, polypropylene, polyethylene glycol, polystyrene, polyvinyl chloride and polyethylene, etc. Surface active agents include cationic surfactants, anionic surfactants and nonionic surfactants. The alkaline source can be divided into organic or inorganic alkali, in which organic alkali can be urea, quaternary ammonium hydroxides compounds, aliphatic amines, alcohols amines and the mixture of these compounds; inorganic alkali can be ammonia, sodium hydroxide, potassium hydroxide, barium hydroxide and the mixture of these compounds.

Patent CN1260241 (application date Apr. 10, 1998, application number 98101357.0) discloses a modification method using alkaline hydrolysis of titanium source solution. In this method, according to the ratio of hydrolysis of titanium source solution:TS-1 sample=200-1500:1, the mixture was crystalized in reactor for 1-8 days under 120-180° C., then TS-1 with extra Ti was obtained after filtration, wash and drying. The alkaline solution can be quaternary ammonium alkali compounds, aliphatic amines and alcohols amines, or the mixture of these compounds.

Patent CN1421389A (application date Nov. 29, 2001, application Ser. No. 01/140,182.6) disclose a modification method using alkaline solution of silicon. In this method, according to the ratio of aqueous solution of silicon:TS=70-1500:1, the mixture was reacted in reactor for 0.1-150 h under 120-180° C., then silicon-modified TS-1 was obtained after filtration, wash and drying. The alkaline solution can be quaternary ammonium base compounds, aliphatic amines and alcohols amines, or the mixture of these compounds.

Patent CN101850986A (application date Mar. 31, 2009, application number 200910131992.0) disclose a modification method using mixed alkaline solution (organic and inorganic). In this method, according to the ratio of TS-1:inorganic alkalin:organic alkalin:water=100 g:(0.005-5 g):(0.01-10 mol):(200-10000 mol), the mixture was reacted for 2-360 h under 80-200° C. and autogenous pressure. Organic alkali can be urea, quaternary ammonium hydroxides compounds, aliphatic amines, alcohols amines and the mixture of these compounds; inorganic alkali can be ammonia, sodium hydroxide, potassium hydroxide, barium hydroxide and the mixture of these compounds. And the ratio of organic and inorganic alkali is 1-50:1.

The following publications also report a modification method for TS-1 by using organic alkaline solution.

Microporous and Mesoporous Materials 102 (2007) 80-85 reported a modification method by using aqueous solution of tetrapropylammonium hydroxide. In this method, TS-1 sample (1 g) was added into the mixed aqueous solution of 4.17 ml TPAOH (1M) and 3.32 ml water, then crystalized under static condition and 170° C. for 24 h. After filtration, wash and drying, modified TS-1 was calcinated for 16 h under 520° C.

The mater dissertation by Baoji Zhang titled "The Study About Synthesis of TS-1, Alkali Modification, Extrusion and Catalytic oxidation of cyclohexane" reported a modification method by using organic alkaline solution. In this method, the organic alkaline solution included TPAOH, ethanolamine, ammonia, hexamethylene tetramine, tetraethyl ammonium hydroxide, the mixture of ammonia and TPABr, the mixture of tetraethyl ammonium hydroxide and TPABr. It is worth mentioning that the catalytic performance has been improved more than twice by using TPAOH. And the catalytic performance has been nearly doubled by using the mixture of ammonia and TPABr, the mixture of tetraethyl ammonium hydroxide and TPABr.

The mater dissertation by Janbo Yin titled "The Optimization of Styrene Epoxidation with $H_2O_2$ on TS-1" reported a modification method for TS-1 by using organic, inorganic alkaline solution and alkaline salts. In this method, TS-1 sample was added into the solution of organic, inorganic and salts to react for 24 h. Then modified TS-1 was obtained after filtration, wash, dry under 100° C. and calcination for 6 h under 540° C. The salt includes $Na_2CO_3$, sodium citrate, sodium acetate and $NaNO_3$. The organic alkali includes TPAOH, tetraethyl ammonium bromide (salt), triethanolamine, propylamine and urea. It is worth mentioning that the modification using inorganic alkaline solution and salt was not good as that by using organic alkaline solution. The only effect of salt during the modification was the cation as inhibitors of acidity.

Many public literatures have reported a modification by using organic alkaline solution, such as many mater dissertations "Synthesis and Modification of Titanium Silicalite-1 and its Performance in Ammoxidation of Methyl Ethyl Ketone" by Lizhen Xia, "Characterization of Titallium Silicalite-1 modified by organic base and its performance in Ammoxidation of Methyl Ethyl Ketone" by Peng Li, "Oxidative Desulfurization of Sulfide over Titanium Siliealite" by Lixia Zhao, "The characters and catalysis activities of micro-TS-1 modified by several kind of Alkali" by Jingbo Mao, "Effect Factors in Synthesis Process of TS-1 Zeolite" by Yang Liu, "The Effect of Modification on TS-1 and Gas-Phase Epoxidation of Propylene" by Guanghong Liu, "The synthesis of TS-1 and catalytic performance in propylene epoxidation" by Xinxu Liu, and some references, such as Acta Petrolei Sinica 2008 24(1) 57-62, Journal of Fuel Chemistry and Technology 2008 36(4)484-488. In this method, alkaline solution includes TMAOH, TEAOH, TPAOH (best modification effect), TBAOH, NaOH, $NH_3$ and $Na_2CO_3$, etc.

To sum up, the effect of inorganic alkaline solution for TS-1 treatment is to dissolve the framework of TS-1, and then internal cavities in TS-1 were generated. General organic bases such as aliphatic amines and alkanolamines have similar performance as inorganic alkali, but quaternary ammonium bases not only can dissolve the framework of zeolite, but also can make dissolved silicon titanium species re-crystalized resulting in some non-framework titanium into framework of zeolite. It is generally thought the effect of treatment of TPAOH for TS-1 is better than that of other quaternary ammonium alkalis. However, the TPAOH treatment has application issue. Besides TS-1 sample synthesized by classic methods and some low-cost methods, not all TS-1 sample can be modified well. The main reasons which cause this phenomenon is big crystal and many amorphous non-framework titanium species in low-cost synthesized TS-1 sample. These two reasons would result in big diffusion resistance, because of longer diffusion path for dissolved titanium species during modification. Furthermore, titanium species in solution is favorable to form $TiO_2$ (anatase). Therefore, the activity of many low-cost synthesized TS-1 after TPAOH modification is not significant improved.

SUMMARY OF THE INVENTION

The goal of this invention is to solve the modification of TS-1 with low cost method based on the mixture of quaternary ammonium salt and inorganic alkali, the catalyst after modification showed better catalytic performance on both gas or liquid phase epoxidation of propylene than before. The key of the patent is using the alkali mixture of quaternary ammonium salt and inorganic alkali replace the alkali metal salts and TPAOH to modify TS-1. It was found that the limitations of the TS-1 modification can be solved by the use of TPAOH and alkali salts, it means that the TS-1 synthesized by classic and low cost method can be modified by TPAOH and alkali salts mixture. Because the cation of alkali salts and the titanic acid radical ion can form the monodisperse or oligomeric ion pairs, the ion pairs could avoid the condensation from titanium acid radical ions to anatase $TiO_2$. The ion pairs was important to the modification of TS-1 synthesized by low cost method, under the low cost method, the micro-sized TS-1 particles was obtained, the attraction of OH— ions to the framework resulted in the Si and Ti species brush off from the inner defective sites of the crystal, the strong interaction between alkali salts and the Ti species avoid the polymerization of $TiO_2$, and led to much more Ti species shift from the crystal of micro-sized TS-1 synthesized by low cost method, and reform back into the framework. It was found that the Ti—O—Ti framework structure (Raman peak at 850 cm-1) was obtained after the modification of TPAOH and alkali salts, Ti—O—Ti framework could transport to high active Ti species during the reaction, therefore the modification of TPAOH and alkali salts was benefit to promote the activity of TS-1.

DETAILED DESCRIPTION OF THE INVENTION

Introduction

First step, pretreatment of TS-1. Pretreatment means that the removal of template under high temperature in air or protective gas. During the pretreatment, the calcination temperature is normally between 300 to 700° C., 400 to 600° C. is preferred; the calcination time is between 30 min to 200 h, 3 to 24 h is preferred. The aim of calcination is to remove the organic template existed in the channel, the blockage of the template in the channels can reject the decomposition and the recrystallization of alkaline liquor to the TS-1. The TS-1 zeolite can obtain from the public references and patents that mentioned in the technology background by hydrothermal synthesis. Any of the engineer who is familiar with this field could prepared the TS-1 that used in this innovation.

Second step, the modification of TS-1 after pretreatment by the mixture of quaternary ammonium salts and inorganic alkali. The quaternary ammonium salts mentioned above include tetrapropyl ammonium fluoride, tetrapropylammonium chloride, tetrapropylammonium iodide and their mixture. The inorganic alkali include that LiOH, NaOH and KOH and their mixture. During the modification, when the ratio of TS-1 to $TPA^+$ salt to alkali salts to $H_2O$ set as TS-1/g:$TPA^+$ salt/mol:salts/g:$H_2O$/g=50:0.005-50:0.05-5: 200-2000, the best catalytic activity could achieve after modification. The treatment was performed in the reactor under the temperature between 50 to 250° C. for 2 h to 10 days. The modification could carry out under stirring or static state, the stirring rate is able to keep the concentration and temperature of the liquid is better.

Third step, the aftertreatment of TS-1 is performed after the modification. The aftertreatment include separation, wash, dry and calcination. Wash is carried out with deionized water until the ph value between 7 to 9; Dry is performed in air or protective gas, the temperature is between 200 to 500° C. for about 1 to 100 h, but 3 to 10 h is preferred. The remain alkali cations would affect the modification result when the ph value of filter liquor above 9. TS-1 shows bad stability and activity when the TS-1 after modification was uncalcined or calcined out of the temperature between 200 to 500° C.

The benefit of the invention is universal capable to modify the TS-1 synthesized by any method, specially the TS-1 with low cost method, the modification can enhance the catalytic performance on both gas and liquid phase epoxidation of propylene

EXAMPLES

Hereinafter, the present invention will further specifically be described with respect to examples, but the present invention is not limited to these examples.

Comparative Example 1

First step, the TS-1 synthesized by classic method (U.S. Pat. No. 4,410,501) was calcined at 540° C. in air for 6 h to remove the template.

Second step, the classic TS-1, TPAOH and water were mixed with a ration is TS-1/g:TPAOH/mol:$H_2O$=50:0.035: 500. Then the mixture was modified under 170° C. for 24 h statically.

Third step, the TS-1 obtained from second step is filtered by deionized water to pH about 7, then calcined at 390° C. for 6 h after dry.

The TS-1 before and after modification catalytic performance of gas phase epoxidation of propylene was carried out as the open literature (Chinese Journal of catalysis, 31(2010)1195-1199) description. Reaction conditions: the flow of $H_2$, $O_2$ and propylene is 170 ml/min, 8 ml/min and 18 ml/min (the molar ratio of $H_2$ to $O_2$ to $C_3$=170/8/18), the amount of TS-1 is 0.8 g (WHSV$C_3$=2.53 h$^{-1}$), the temperature is 110° C. The main evaluation parameters of gas-solid phase epoxidation of propylene are the conversion of $C_3H_6$ and the selectivity of PO. The reaction results showed that the conversion of $C_3H_6$ and the selectivity of PO is 4.6% and 91.2 respectively over the TS-1 before modification, 7.9% and 94.2% over the TS-1 after modification.

Comparative Example 2

Repeat the compared example 1, but the TS-1 sample with big crystal modified was synthesized by the open literature of Appl. Catal. A, 185, (1999) 11 under low cost method. The epoxidation results displayed that the conversion of $C_3H_6$ and the selectivity of PO is 4.5% and 78.4 respectively over the TS-1 before modification, 5.2% and 82.2% over the TS-1 after modification.

Comparative Example 3

Repeat the compared example 1, the liquid phase epoxidation of propylene was carried out under the reaction conditions as follows: a 400 ml uncontinuous stainless-steel high pressure reactor; the catalyst is 0.2 g, the methanol is 30 ml and 30 wt % $H_2O_2$ was 2 ml; the propylene is introduced under stirring and the $C_3H_6$ is charged at constant pressure (0.4 Mpa); reaction temperature is 50° C.; reaction time is 60 min; the conversion of $H_2O_2$ is measured by the iodometric titration. The selectivity of PO and utilization of $H_2O_2$ is analyzed on a chromatography. The TS-1 before modification showed 76.3% of $H_2O_2$ conversion, 78.8% of PO selectivity and 78.2% utilization of $H_2O_2$; 87.2% of $H_2O_2$ conversion, 91.3% of PO selectivity and 89.5% utilization of $H_2O_2$ over the TS-1 after modification.

Example 1

First step, the TS-1 sample with big crystal modified was synthesized by the open literature of Appl. Catal. A, 185, (1999) 11 under low cost method, and then calcined at 540° C. in air for 6 h to remove the template.

Second step, the cheap TS-1, TPAOH, sodium bromide and water were mixed with a ratio is TS-1/g:TPAOH/mol:salt/g:$H_2O$=50:0.035:1.4:500. Then the mixture was modified under 170° C. for 24 h statically in a reactor.

Third step, the TS-1 obtained from second step was filtered by deionized water to pH of about 7, calcined at 390° C. for 6 h after dry. The TS-1 before and after modification catalytic performance of gas phase epoxidation of propylene was carried out as the open literature (Chinese Journal of catalysis, 31(2010)1195-1199) description. Reaction conditions: the flow of $H_2$, $O_2$ and propylene is 170 ml/min, 8 ml/min and 18 ml/min (the molar ratio of $H_2$ to $O_2$ to $C_3$=170/8/18), the amount of TS-1 is 0.8 g (WHSV$C_3$=2.53 $h^{-1}$), the temperature is 110° C. The main evaluation parameters of gas-solid phase epoxidation of propylene were the conversion of $C_3H_6$ and the selectivity of PO. The reaction results showed that the conversion of $C_3H_6$ and the selectivity of PO is 4.5% and 78.4% respectively over the TS-1 before modification, 8.8% and 99.2% over the TS-1 after modification.

Example 2

Repeated the example 1, but the TS-1 was synthesized under classic system (U.S. Pat. No. 4,410,501). The results showed that the conversion of $C_3H_6$ and the selectivity of PO is 4.6% and 91.2% respectively over the TS-1 before modification, 9.5% and 99.4% over the TS-1 after modification.

Example 3

Repeated the example 1, the liquid phase epoxidation of propylene was carried out under the reaction conditions as follows: a 400 ml uncontinuous stainless-steel high pressure reactor; the catalyst is 0.2 g, the methanol is 30 ml and 30 wt % $H_2O_2$ is 2 ml; the propylene is introduced under stirring and the $C_3H_6$ is charged at constant pressure (0.4 Mpa); reaction temperature is 50° C.; reaction time is 60 min; the conversion of $H_2O_2$ is measured by the iodometric titration. The selectivity of PO and utilization of $H_2O_2$ was analyzed on a chromatography. The TS-1 before modification showed 72.7% of $H_2O_2$ conversion, 73.4% of PO selectivity and 68.8% utilization of $H_2O_2$; 89.2% of $H_2O_2$ conversion, 91.5% of PO selectivity and 93.4% utilization of $H_2O_2$ over the TS-1 after modification.

Example 4

Repeated the example 1, the sodium bromide was replaced by equal lithium bromide, potassium bromide, lithium chloride, sodium chloride, potassium chloride, lithium carbonate, sodium carbonate and potassium carbonate. The epoxidation results were as follows: the TS-1 before modification showed 4.5% of $C_3H_6$ conversion and 78.4% of PO selectivity; 8.1% of $C_3H_6$ conversion and 99.1% of PO selectivity over TS-1 after lithium bromide modification; 8.1% of $C_3H_6$ conversion and 98.9% of PO selectivity over TS-1 after potassium bromide modification; 8.0% of $C_3H_6$ conversion and 99.0% of PO selectivity over TS-1 after lithium chloride modification; 8.1% of $C_3H_6$ conversion and 99.1% of PO selectivity over TS-1 after sodium chloride modification; 8.2% of $C_3H_6$ conversion and 99.0% of PO selectivity over TS-1 after potassium chloride modification; 8.1% of $C_3H_6$ conversion and 99.1% of PO selectivity over TS-1 after lithium carbonate modification; 8.2% of $C_3H_6$ conversion and 98.5% of PO selectivity over TS-1 after sodium carbonate modification; 7.8% of $C_3H_6$ conversion and 99.0% of PO selectivity over TS-1 after potassium carbonate modification.

Example 5

Repeated the example 1, the sodium bromide was replaced equally by lithium bromide and potassium bromide (ratio=1:1), sodium chloride and potassium chloride (ratio=1:4), sodium carbonate and potassium carbonate (ratio=1:2) mixture. The epoxidation results were as follows: the TS-1 before modification showed 4.5% of $C_3H_6$ conversion and 78.4% of PO selectivity; 7.9% of $C_3H_6$ conversion and 99.2% of PO selectivity over TS-1 after lithium bromide and potassium bromide (ratio=1:1) modification; 7.8%1 of $C_3H_6$ conversion and 98.8% of PO selectivity over TS-1 after sodium chloride and potassium chloride (ratio=1:4) modification; 7.6% of $C_3H_6$ conversion and 99.3% of PO selectivity over TS-1 after sodium carbonate and potassium carbonate (ratio=1:2) modification.

Example 6

Repeated the example 1, the sodium hydroxide was replaced equally by lithium hydroxide and potassium hydroxide. The epoxidation results were as follows: the TS-1 before modification shows 4.5% of $C_3H_6$ conversion and 78.4% of PO selectivity; 8.7% of $C_3H_6$ conversion and 99.1% of PO selectivity over TS-1 after lithium hydroxide modified; 8.8% of $C_3H_6$ conversion and 99.5% of PO selectivity over TS-1 after lithium hydroxide modified.

Example 7

Repeated the example 1, the sodium hydroxide was replaced by equimolar lithium hydroxide and potassium hydroxide (1:1) or sodium hydroxide and potassium hydroxide (1:4) mixture. The epoxidation results were as follows: the TS-1 before modification shows 4.5% of $C_3H_6$ conversion and 78.4% of PO selectivity; 8.8% of $C_3H_6$ conversion and 99.1% of PO selectivity over TS-1 after lithium hydroxide and potassium hydroxide (1:1) mixture modified; 8.7% of $C_3H_6$ conversion and 99.6% of PO selectivity over TS-1 after sodium hydroxide and potassium hydroxide (1:4) mixture modified.

Example 8

Repeated the example 1, change the amount of terapropylammonium bormide, so that the TS-1, TPABr, sodium hydroxide and water were mixed with the ratio of TS-1/g: TPABr/mol:NaOH/g:$H_2O$=50:0.005:1.4:500 and 50:50:1.4: 500. The epoxidation results were as follows: the TS-1 before modification shows 4.5% of $C_3H_6$ conversion and 78.4% of PO selectivity; 6.8% of $C_3H_6$ conversion and 94.1% of PO selectivity over the TS-1 modified with the former ratio; 5.8% of $C_3H_6$ conversion and 92.1% of PO selectivity over the TS-1 modified with the later ratio.

Example 9

Repeated the example 1, change the amount of sodium hydroxide, so that the TS-1, TPABr, sodium hydroxide and water were mixed with the ratio of TS-1/g:TPABr/mol: NaOH/g:$H_2O$=50:0.035:1.4:500 and 50:0.035:5:500. The epoxidation results were as follows: the TS-1 before modification showed 4.5% of $C_3H_6$ conversion and 78.4% of PO selectivity; 5.8% of $C_3H_6$ conversion and 92.1% of PO selectivity over the TS-1 modified with the former ratio; 4.8% of $C_3H_6$ conversion and 99.9% of PO selectivity over the TS-1 modified with the later ratio;

Example 10

Repeated the example 1, change the amount of water, so that the TS-1, TPABr, sodium hydroxide and water were mixed with the ratio of TS-1/g:TPABr/mol:NaOH/g: $H_2O$=50:0.035:1.4:200 and 50:0.035:1.4:2000. The epoxidation results were as follows: the TS-1 before modification shows 4.5% of $C_3H_6$ conversion and 78.4% of PO selectivity; 7.8% of $C_3H_6$ conversion and 98.1% of PO selectivity over the TS-1 modified with the former ratio; 5.8% of $C_3H_6$ conversion and 91.9% of PO selectivity over the TS-1 modified with the later ratio.

Example 11

Repeated the example 1, the modification was carried out under stirring. TS-1 before modification shows 4.5% of $C_3H_6$ conversion and 78.4% of PO selectivity; TS-1 after modification under stirring displays 8.8% of $C_3H_6$ conversion and 98.8% of PO selectivity.

Example 12

Repeated the example 1, the epoxidation was performed over the TS-1 with pretreated temperature is 300° C., 400° C., 600° C. and 700° C. TS-1 before modification showed 4.5% of $C_3H_6$ conversion and 78.4% of PO selectivity; TS-1 pretreated at 300° C. displayed 7.4% of $C_3H_6$ conversion and 93.3% of PO selectivity; TS-1 pretreated at 400° C. displayed 8.7% of $C_3H_6$ conversion and 96.5% of PO selectivity; TS-1 pretreated at 600° C. displayed 8.6% of $C_3H_6$ conversion and 97.7% of PO selectivity; TS-1 pretreated at 700° C. displayed 7.8% of $C_3H_6$ conversion and 92.4% of PO selectivity.

Example 13

Repeated the example 1, the TS-1 pretreated time was change to 30 min, 3 h, 24 h and 200 h. TS-1 before modification showed 4.5% of $C_3H_6$ conversion and 78.4% of PO selectivity; TS-1 pretreated for 30 min displayed 7.4% of $C_3H_6$ conversion and 93.7% of PO selectivity; TS-1 pretreated for 3 h displayed 8.2% of $C_3H_6$ conversion and 95.7% of PO selectivity; TS-1 pretreated for 24 h displayed 8.5% of $C_3H_6$ conversion and 96.5% of PO selectivity; TS-1 pretreated for 200 h displayed 7.2% of $C_3H_6$ conversion and 94.5% of PO selectivity.

Example 14

Repeated the example 1, the TS-1 modified temperature was change to 50° C. and 250° C. TS-1 before modification showed 4.5% of $C_3H_6$ conversion and 78.4% of PO selectivity; TS-1 modified at 50° C. displayed 6.8% of $C_3H_6$ conversion and 92.8% of PO selectivity; TS-1 modified at 250° C. displayed 5.8% of $C_3H_6$ conversion and 91.1% of PO selectivity.

Example 15

Repeated the example 1, the TS-1 modified time was change to 2 h and 10 d. TS-1 before modification showed 4.5% of $C_3H_6$ conversion and 78.4% of PO selectivity; TS-1 modified for 2 h displayed 4.9% of $C_3H_6$ conversion and 91.0% of PO selectivity; TS-1 modified for 10 d displayed 8.0% of $C_3H_6$ conversion and 96.1% of PO selectivity.

Example 16

Repeated the example 1, the pH value in the step 3 was set at 9. TS-1 before modification showed 4.5% of $C_3H_6$ conversion and 78.4% of PO selectivity; TS-1 after such modification displayed 5.7% of $C_3H_6$ conversion and 99.9% of PO selectivity.

Example 17

Repeated the example 1, the dry temperature in the step 3 was changed to 60° C. and 250° C. TS-1 before modification showed 4.5% of $C_3H_6$ conversion and 78.4% of PO selectivity; TS-1 dried at 60° C. displayed 8.7% of $C_3H_6$ conversion and 97.9% of PO selectivity; TS-1 dried at 250° C. displayed 4.7% of $C_3H_6$ conversion and 97.9% of PO selectivity.

Example 18

Repeated the example 1, the dry time in the step 3 was changed to 1 h and 100 h. TS-1 before modification showed 4.5% of $C_3H_6$ conversion and 78.4% of PO selectivity; TS-1 dried for 1 h displayed 8.3% of $C_3H_6$ conversion and 94.9% of PO selectivity; TS-1 dried for 100 h displayed 8.8% of $C_3H_6$ conversion and 97.8% of PO selectivity.

Example 19

Repeated the example 1, the calcination temperature in the step 3 was changed to 200° C. and 500° C. TS-1 before modification showed 4.5% of $C_3H_6$ conversion and 78.4% of PO selectivity; TS-1 calcined at 200° C. displayed 8.3% of $C_3H_6$ conversion and 94.9% of PO selectivity; TS-1 calcined at 500° C. displayed 8.8% of $C_3H_6$ conversion and 97.8% of PO selectivity.

Example 20

Repeated the example 1, the calcination time in the step 3 was changed to 30 min and 100 h. TS-1 before modification showed 4.5% of $C_3H_6$ conversion and 78.4% of PO selectivity; TS-1 calcined for 30 min displayed 8.6% of $C_3H_6$ conversion and 97.9% of PO selectivity; TS-1 calcined for 100 h displayed 8.8% of $C_3H_6$ conversion and 97.8% of PO selectivity.

We claim:

1. A modification method of Titanium-silicalite (TS-1) comprising:
providing an amount of TS-1;
pretreating the TS-1 by performing calcination of the TS-1 either under atmosphere or protective gas, wherein a calcination temperature is between 300 to 700° C., and a calcination time is between 30 min to 200 h;
performing modification of the TS-1 using a mixture of quaternary ammonium salts and inorganic alkali, wherein the quaternary ammonium salts are selected from the group consisting of tetrapropylammonium fluoride, tetrapropylammonium chloride, tetrapropylammonium iodide and combinations thereof, and wherein the inorganic alkali are selected from the group consisting of LiOH, NaOH, KOH and combinations thereof, and the treatment is performed in a reactor at a temperature between 50 and 250° C. for 2 h to 10 days; and
performing aftertreatment of the TS-1 by a process of separation, washing, and drying, wherein washing is carried out with deionized water and the drying is performed under atmosphere or protective gas at a temperature between 200 and 500° C. for 1 to 100 h.

2. The method of claim 1, in the calcination temperature is between 400 and 600° C., and the calcination time is between 3 h to 24 h during the step of pretreating.

3. The method of claim 1, wherein a ratio of TS-1 to TPAOH to salts to $H_2O$ is TS-1/g:TPAOH/mol:salts/g:$H_2O$/g=50:0.005-50:0.05-5:200-2000 during the step of modification.

4. The method of claim 1, wherein the pH of the TS-1 is adjusted to a value between 7 and 9 during the step of aftertreatment.

5. The method of claim 1, wherein a calcination step is performed after drying during the aftertreatment step at a temperature between 200 and 500° C. for 30 min to 100 h.

* * * * *